(12) United States Patent
Arce et al.

(10) Patent No.: US 8,486,035 B1
(45) Date of Patent: Jul. 16, 2013

(54) OSTOMY UNDERGARMENT

(71) Applicants: Hector F. Arce, Haverhill, MA (US); Brian O. Mohika, Haverhill, MA (US)

(72) Inventors: Hector F. Arce, Haverhill, MA (US); Brian O. Mohika, Haverhill, MA (US)

( * ) Notice: Subject to any disclaimer, the term of this patent is extended or adjusted under 35 U.S.C. 154(b) by 0 days.

(21) Appl. No.: 13/673,481

(22) Filed: Nov. 9, 2012

(51) Int. Cl.
| | |
|---|---|
| *A61F 5/44* | (2006.01) |
| *A41D 13/00* | (2006.01) |
| *A41D 15/00* | (2006.01) |
| *A41D 1/22* | (2006.01) |
| *A41D 11/00* | (2006.01) |
| *A41D 1/06* | (2006.01) |
| *A41D 13/02* | (2006.01) |
| *A41D 1/08* | (2006.01) |
| *A41B 13/06* | (2006.01) |
| *A41B 9/08* | (2006.01) |
| *A41B 9/00* | (2006.01) |
| *A41B 9/14* | (2006.01) |
| *A41B 1/00* | (2006.01) |
| *A41B 11/04* | (2006.01) |
| *A41B 11/00* | (2006.01) |
| *A41F 9/00* | (2006.01) |

(52) U.S. Cl.
USPC ........... 604/345; 604/326; 604/327; 604/343; 604/349; 604/351; 604/353; 2/69; 2/70; 2/71; 2/72; 2/73; 2/74; 2/75; 2/76; 2/77; 2/78; 2/79; 2/80; 2/81; 2/82; 2/83; 2/400; 2/401; 2/402; 2/403; 2/404; 2/405; 2/406; 2/407; 2/408; 2/227; 2/228; 2/229; 2/230; 2/231; 2/232; 2/233; 2/234; 2/235; 2/236; 2/237; 2/238; 2/239; 2/240; 2/241; 2/242

(58) Field of Classification Search
USPC .............. 604/345, 326, 327, 343, 349, 351, 604/353; 2/69–83, 400–409, 227–242
See application file for complete search history.

(56) References Cited

U.S. PATENT DOCUMENTS

| | | | |
|---|---|---|---|
| 4,820,291 A | 4/1989 | Terauchi et al. | |
| 4,888,006 A | 12/1989 | Beaupied | |
| 5,032,118 A | 7/1991 | Mason | |
| D395,356 S | 6/1998 | Tang | |
| 6,110,156 A | 8/2000 | Mendonca | |
| 6,178,559 B1 * | 1/2001 | Dennis et al. | 2/400 |
| 6,468,254 B2 | 10/2002 | Gupton | |
| 6,544,232 B1 * | 4/2003 | McDaniel | 604/174 |
| 2005/0075615 A1 * | 4/2005 | Bonham | 604/327 |

* cited by examiner

*Primary Examiner* — Jacqueline Stephens
*Assistant Examiner* — Andrew J Mensh

(57) ABSTRACT

A medical undergarment system effective for supporting an ostomy system consists of a first diagonal catheter channel, a second diagonal catheter channel, a first vertical catheter channel, and a second vertical catheter channel. The system consists of tubing, a base undergarment, and a fluid bag. The medical undergarment system provides a comfortable yet stable ostomy system that can easily be slipped on and off by a user. The system enables convenient and easy removal of bodily fluid when using a catheter.

11 Claims, 5 Drawing Sheets

OSTOMY UNDERGARMENT

BACKGROUND OF THE INVENTION

The present invention generally relates to bodily fluid draining appliances, systems, and devices for supporting ostomy systems. More specifically, the present invention is a medical undergarment system for supporting an ostomy system.

SUMMARY

It is believed that the prior art lacks an effective yet comfortable undergarment incorporating a bodily fluid drainage system. The prior art contains undergarments which, it is believed lack utility and are uncomfortable for the user. As such, there is a need for a stable, comfortable and effective ostomy system.

The present invention features a medical undergarment system for supporting an ostomy system, in some embodiments, the undergarment comprises four catheter tube channels, catheter tubing, a base undergarment, and fluid bags.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
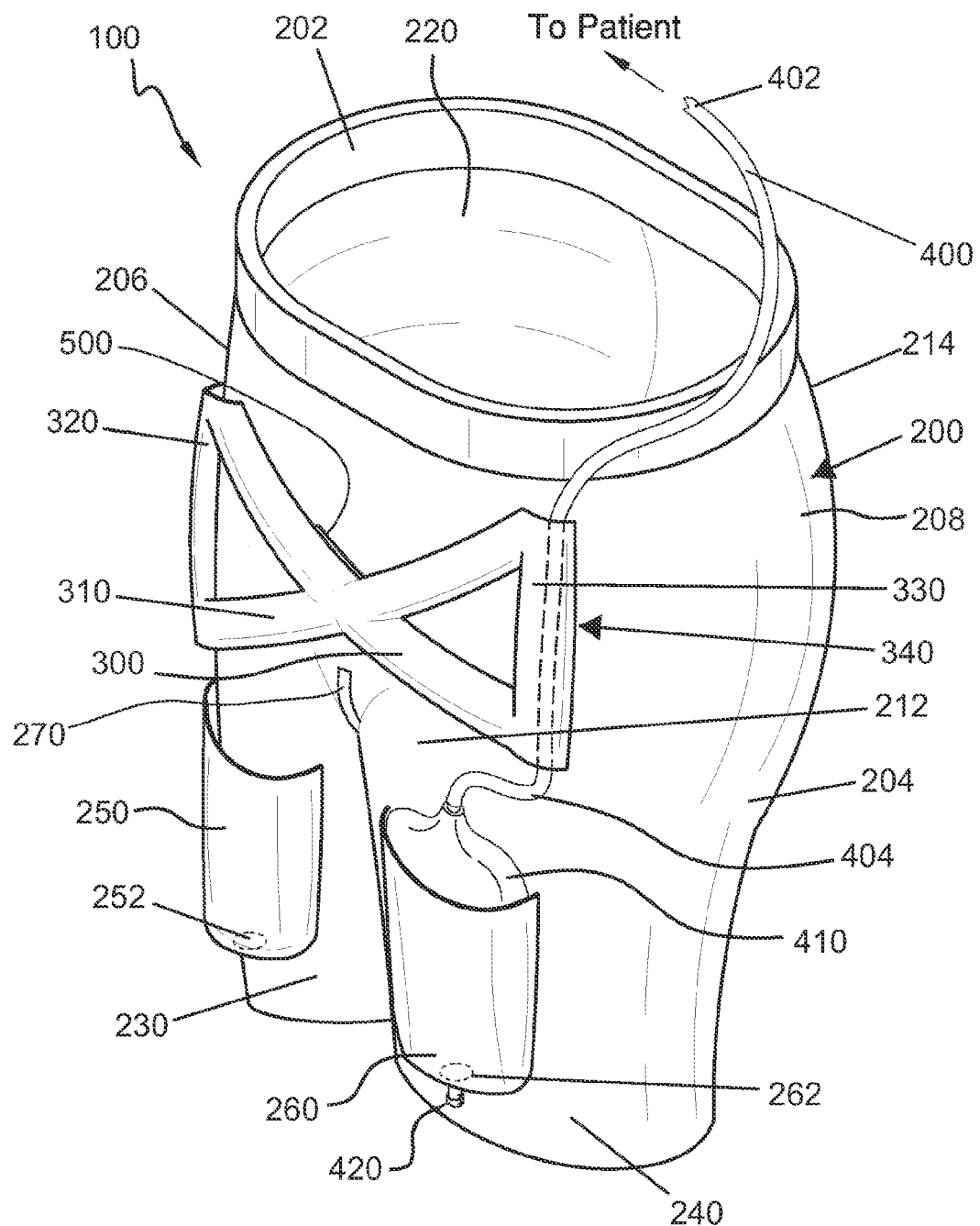
FIG. 1 is a perspective view of the present invention.
Figure 2:
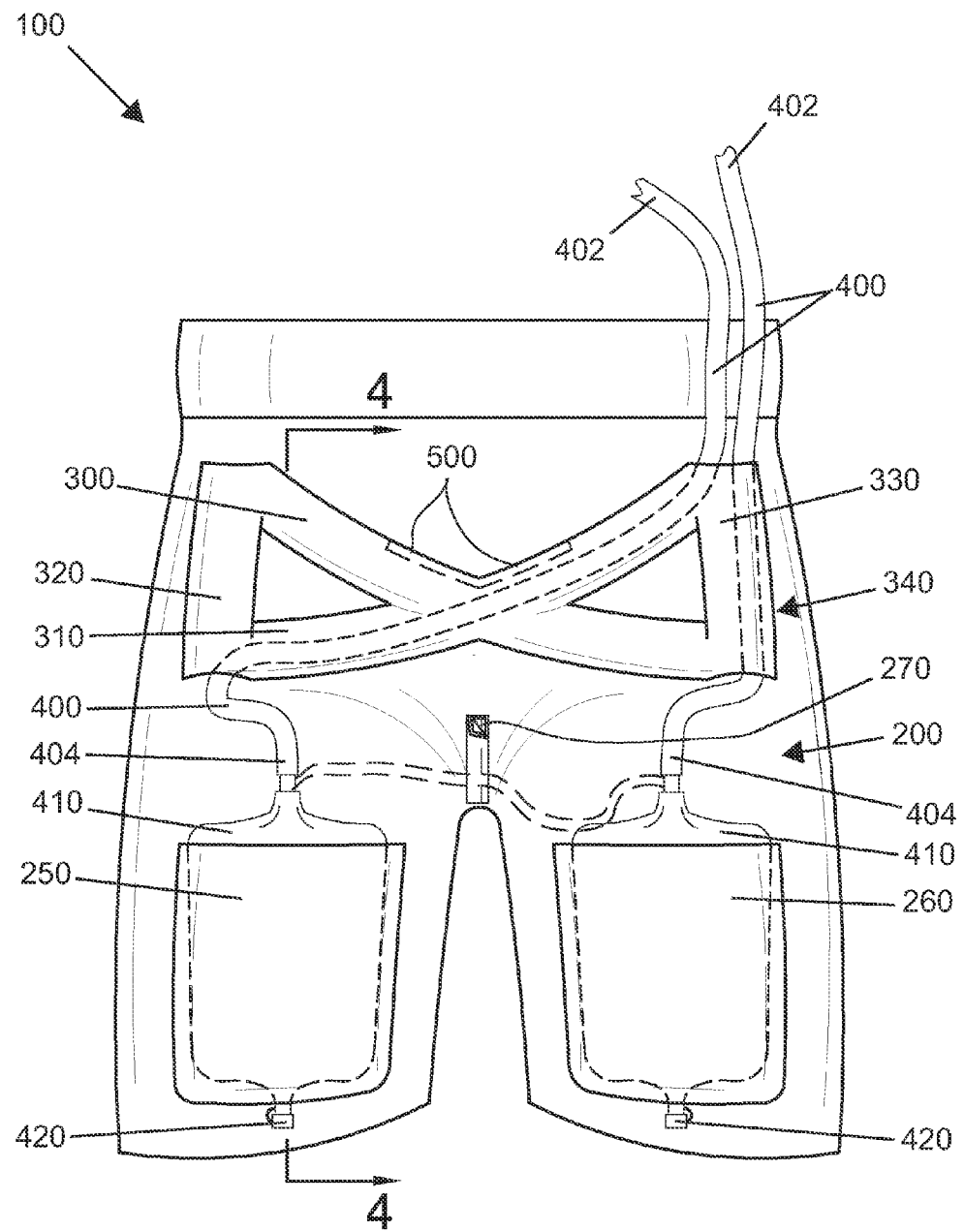
FIG. 2 is a front view of the present invention.
Figure 3:
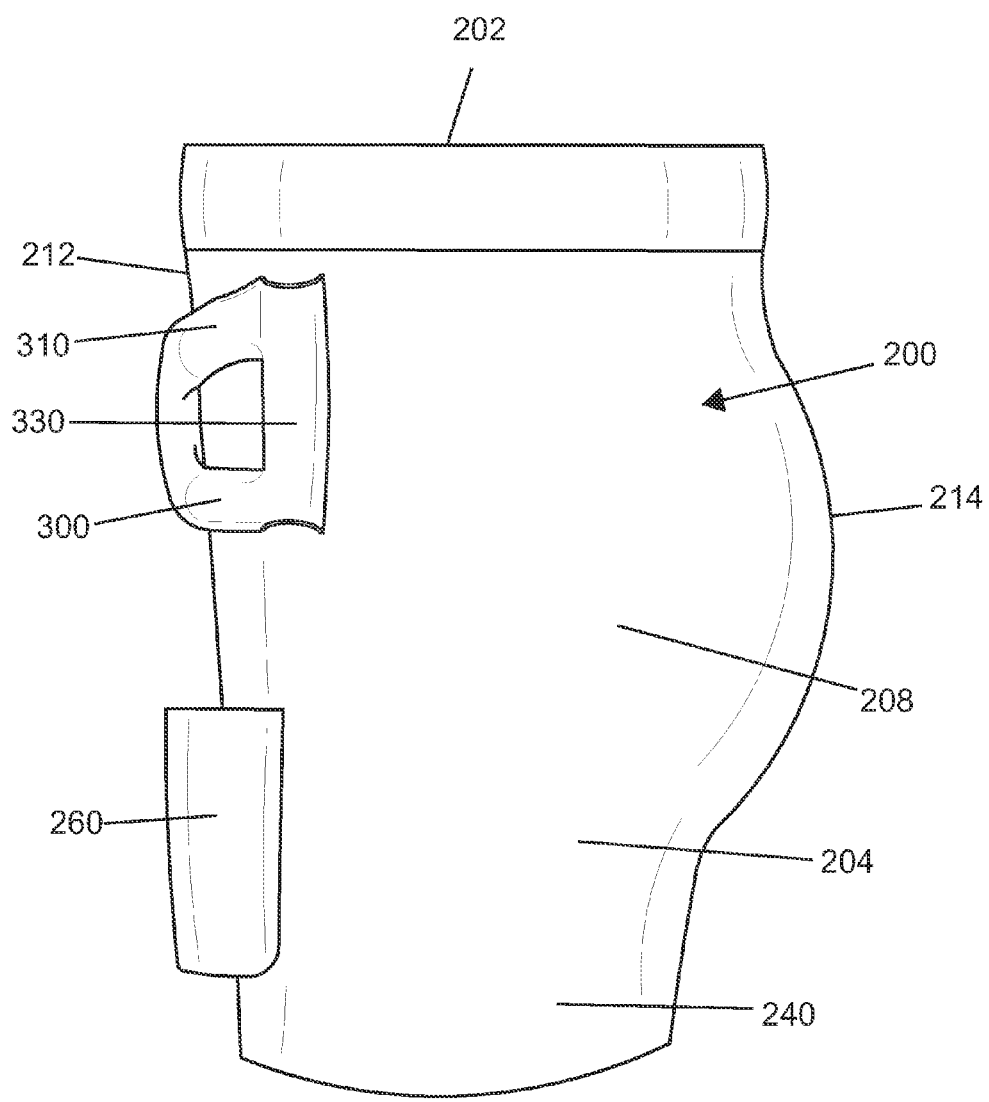
FIG. 3 is a side view of the present invention.
Figure 4:
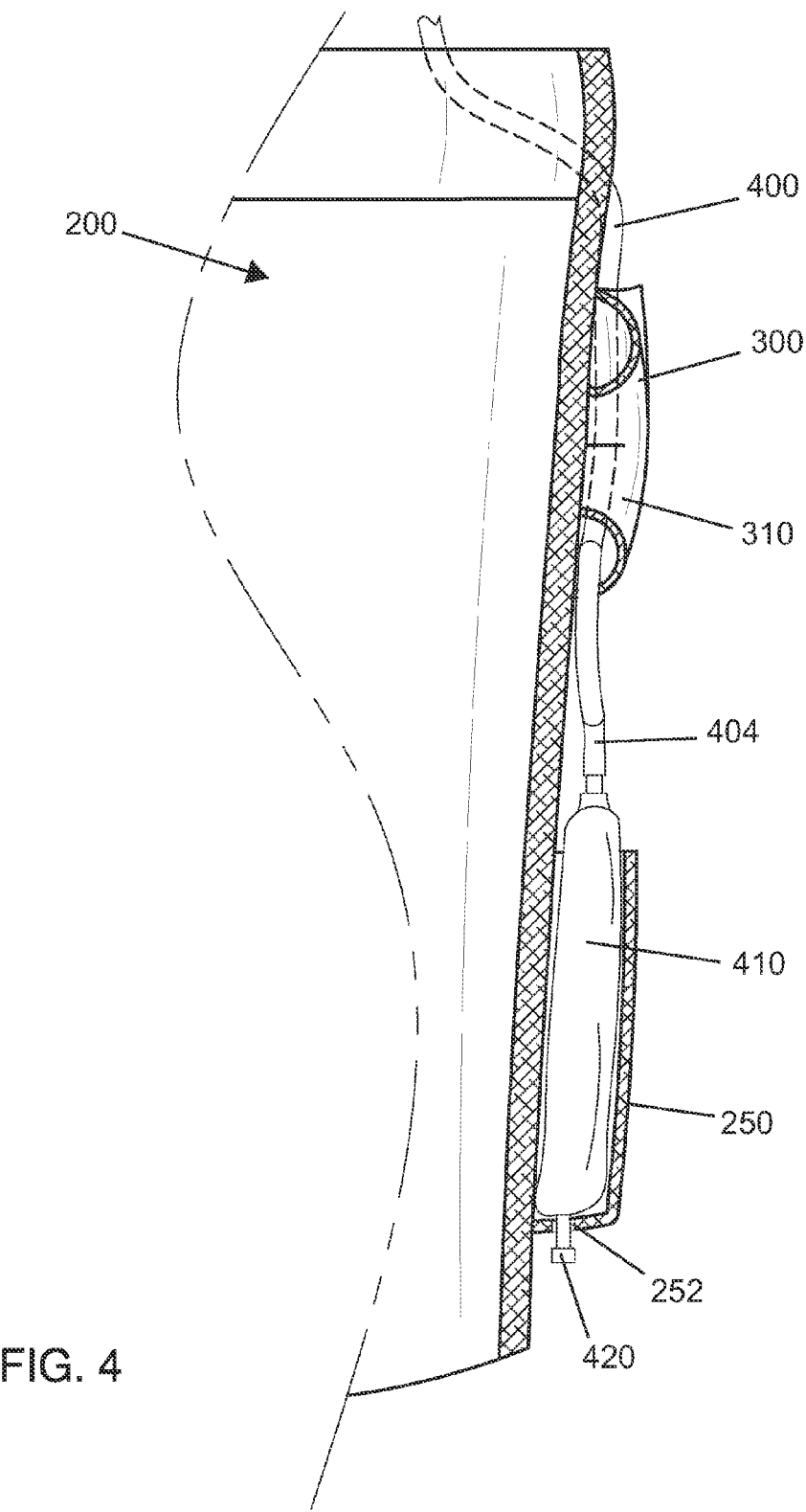
FIG. 4 is a cross-sectional view in a sagittal plane of the present invention.
Figure 5:
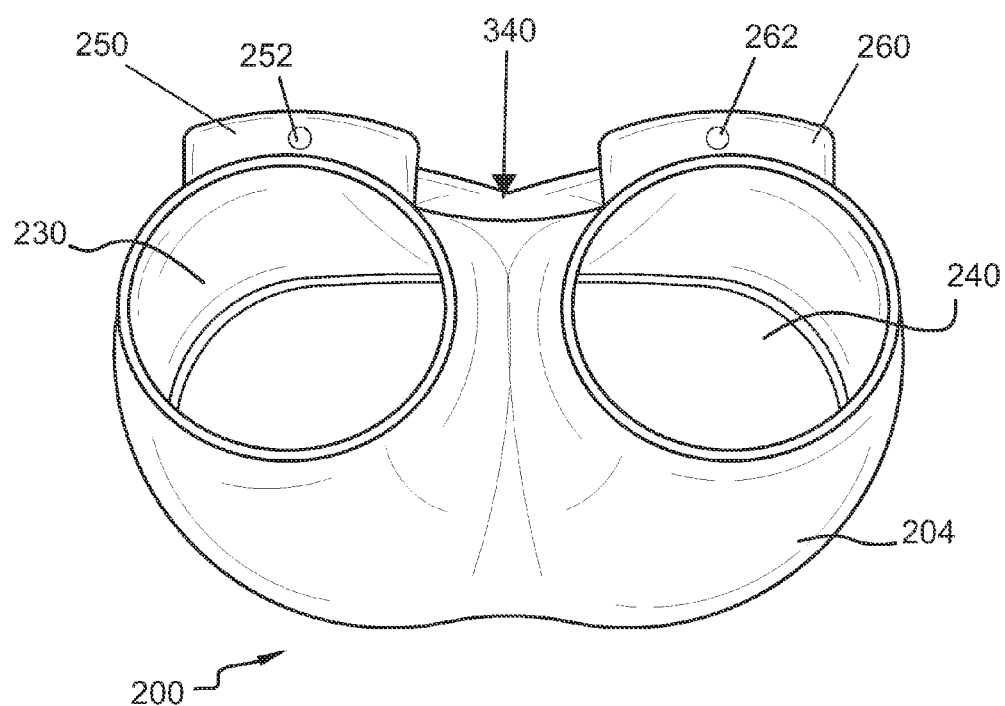
FIG. 5 is a bottom view of the present invention.

Following is a list of elements corresponding to a particular element referred to herein:
100 Medical undergarment system
200 Base undergarment
202 Undergarment top
204 Undergarment bottom
206 Undergarment first side
208 Undergarment second side
212 Undergarment front surface
214 Undergarment rear surface
220 Waist opening
230 First leg extension
240 Second leg extension
250 First pocket
252 First pocket aperture
260 Second pocket
262 Second pocket aperture
270 Lower undergarment aperture
300 First diagonal catheter channel
310 Second diagonal catheter channel
320 First vertical catheter channel
330 Second vertical catheter channel
340 Catheter channel network
400 Catheter tubing
402 Tubing first end
404 Tubing second end
410 Fluid bag
420 Fluid release
500 Access opening Referring now to FIGS. 1-5, the present invention features, in some embodiments, a medical undergarment system effective for supporting an ostomy system.

In some embodiments, the system comprises a base undergarment (200) having a waist opening (220). In some embodiments, the waist opening (220) is of a predetermined size and shape suitable for placing the undergarment on a user. In some embodiments, the base undergarment (200) comprises a first leg extension (230) and a second leg extension (240). In some embodiments, the base undergarment (200) comprises a first pocket (250) located on a front side of the first leg extension (230) and a second pocket (260) located on a front side of the second leg extension (240). In some embodiments, the first pocket (250) has a first pocket aperture (252) and the second pocket (260) has a second pocket aperture (262). In some embodiments, the base undergarment comprises a lower aperture (270) located at a crotch position of the base undergarment (200). In some embodiments, the crotch position is located between and above the first (250) and second (260) pockets, and between the first (250) and second (260) pockets and a lip of the base undergarment.

In some embodiments, the system comprises a first diagonal catheter channel (300) stretching across and attached to a front side of the base undergarment (200). In some embodiments, the first diagonal catheter channel (300) is above the first pocket (250) and the second pocket (260).

In some embodiments, the system comprises a second diagonal catheter channel (310) stretching across and attached to the front side of the base undergarment (200). In some embodiments, the second diagonal catheter channel (310) is above the first pocket (250) and the second pocket (260). In some embodiments, the first (300) and second diagonal catheter channels (310) cross each other at the crotch position and are fluidly connected.

In some embodiments, a catheter tubing (400) is located within the first (300) and second (310) catheter tract channels. In some embodiments, a portion of the catheter tubing (400) comprises a tubing first end (402) located at a crotch portion. In some embodiments, the tubing first end (402) penetrates under the lower aperture (270). In some embodiments, the tubing first end (402) is effective for receipt and connection to a genital of the user.

In some embodiments, the system comprises at least one fluid bag (410) comprising a removable fluid release (420) located on a lower portion of the fluid bag (410). In some embodiments, the fluid bag (420) is adapted to be tucked into the first or second pocket (250) such that the fluid release (420) tab fits through the first pocket aperture (252) if the fluid bag (410) is tucked in the first pocket (250), or the second pocket aperture (262) if the fluid bag (410) is tucked in the second pocket (250).

In some embodiments, the medical urinary undergarment is effective for receiving and disposing of urine by the user where the user slips on the base undergarment (200) and attaches the genital to the tubing first end (402). In some embodiments, when the at least one fluid bag (410) is filled, the user can empty the fluid bag (410) by removing the fluid release (420).

In some embodiments, a medical undergarment system (100) effective for supporting an ostomy system (100) comprises a base undergarment (200) having an undergarment top (202), and undergarment bottom (204), an undergarment first side (206), an undergarment second side (208), an undergarment front surface (212), and an undergarment rear surface (214). In some embodiments, the undergarment top (202) comprises a waist opening (220) having a predetermined size and shape suitable for securing the base undergarment (200) around a waist of a user. In some embodiments, the base undergarment (200) further comprises a first leg extension (230) on the undergarment bottom (204) close to the undergarment first side (206), and a second leg extension (240) on the undergarment bottom (204) close to the undergarment second side (208). In some embodiments, the base undergarment (200) further comprises a first pocket (250) located on the undergarment front surface (212) close to the undergarment first side (206) above the first leg extension (230), and a second pocket (260) located on the undergarment front surface (212) close to the undergarment second side (208) above the second leg extension (240). In some embodiments, the first pocket (250) comprises a first pocket aperture (252) located on a bottom surface thereon. In some embodiments, the second pocket (260) comprises a second pocket aperture (262) located on a bottom surface thereon. In some embodiments, the base undergarment (200) further comprises a lower undergarment aperture (270) located at an undergarment bottom (204) between the first leg extension (230) and the second leg extension (240).

In some embodiments, the system (100) comprises a first diagonal catheter channel (300) located on the undergarment front surface (212). In some embodiments, a first open end is located on the undergarment first side (206) close to the undergarment top (202) and a second open end is located on the undergarment second side (208) close to the undergarment bottom (204).

In some embodiments, the system (100) comprises a second diagonal catheter channel (310) located on the undergarment front surface (212). In some embodiments, a first open end is located on the undergarment second side (208) close to the undergarment top (202) and a second open end is located on the undergarment first side (206) close to the undergarment bottom (204).

In some embodiments, the system (100) comprises a first vertical catheter channel (320) located on the undergarment front surface (212). In some embodiments, a first open end is located on the undergarment first side (206) close to the undergarment top (202) and a second open end is located on the undergarment first side (206) close to the undergarment bottom (204).

In some embodiments, the system (100) comprises a second vertical catheter channel (330) located on the undergarment front surface (212). In some embodiments, a first open end is located on the undergarment second side (208) close to the undergarment top (202) and a second open end is located on the undergarment second side (208) close to the undergarment bottom (204).

In some embodiments, the first diagonal catheter channel (300) and the second diagonal catheter channel (310) are fluidly connected at an intersecting midpoint thereon. In some embodiments, the first open end of the first diagonal catheter channel (300) is fluidly connected to the first open end of the first vertical catheter channel (320) at an intersecting endpoint thereon. In some embodiments, the second open end of the first diagonal catheter channel (300) is fluidly connected to the second open end of the second vertical catheter channel (330) at an intersecting endpoint thereon. In some embodiments, the first open end of the second diagonal catheter channel (310) is fluidly connected to the first open end of the second vertical catheter channel (330) at an intersecting endpoint thereon. In some embodiments, the second open end of the second diagonal catheter channel (310) is fluidly connected to the second open end of the first vertical catheter channel (320) at an intersecting endpoint thereon. In some embodiments, the first diagonal catheter channel (300), the second diagonal catheter channel (310), the first vertical catheter channel (320) and the second vertical catheter channel form a catheter channel network (340).

In some embodiments, the system (100) comprises a length of catheter tubing (400) having a tubing first end (402) and a tubing second end (404). In some embodiments, the catheter tubing (400) is at least partially located within the catheter channel network (340). In some embodiments, the tubing first end (402) is adapted to connect to the user.

In some embodiments, the system (100) comprises a fluid bag (410) having a fluid release (420) located on a lower portion of the fluid bag (410). In some embodiments, the fluid bag (420) is adapted to be enveloped by the first pocket (250) or the second pocket (260). In some embodiments, the fluid release (420) extends through the first pocket aperture (252) or the second pocket aperture (262).

In some embodiments, the medical urinary undergarment is effective for receiving and disposing of fluid by the user. In some embodiments, for use, the user dons the base undergarment (200). In some embodiments, the user attaches the tubing first end (402) to a stoma. In some embodiments, the user routes the catheter tubing (400) through the catheter channel network (340). In some embodiments, the user connects the tubing second end (404) to the fluid bag (410). In some embodiments, the user places the fluid bag (410) in the first pocket (250) or the second pocket (260). In some embodiments, when the fluid bag (410) is filled with fluid, the user can drain the fluid bag (410) via the fluid release (420).

In some embodiments, the base undergarment (200) comprises polyester, cotton, or a polyester and cotton blend. In some embodiments, the base undergarment (200) is adapted to resemble briefs. In some embodiments, the base undergarment (200) is adapted to resemble boxer shorts. In some embodiments, the base undergarment (200) is adapted to resemble spandex underwear. Undergarments and their construction are well know to those of ordinary skill in the art.

In some embodiments, the tubing first end (402) is adapted to connect to a urinary catheter. In some embodiments, the tubing first end (402) is adapted to connect to a percutaneous catheter. In some embodiments, the tubing first end (402) is adapted to connect to a Foley catheter. In some embodiments, the tubing second end (404) is adapted to connect to a plurality of fluid bags (410).

In some embodiments, an access opening (500) is located at the intersecting midpoint of the first diagonal catheter channel (300) and the second diagonal catheter channel (310). In some embodiments, an interior of the catheter channel network (340) can be accessed via the access opening (500). In some embodiments, the access opening (500) is secured via a hook and loop system.

As used herein, the term "about" refers to plus or minus 10% of the referenced number.

As used herein, the term "about" refers to plus or minus 10% of the referenced number. For example, an embodiment wherein the device is about 10 inches in length includes a device that is between 9 and 11 inches in length.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. A medical undergarment system (100) effective for supporting an ostomy system, wherein the undergarment system (100) comprises:
   a. an base undergarment (200) having an undergarment top (202), and undergarment bottom (204), an undergarment first side (206), an undergarment second side (208), an undergarment front surface (212), and an undergarment rear surface (214), wherein the undergarment top (202) comprises a waist opening (220) having a predetermined size and shape suitable for securing the base undergarment (200) on a waist of a user, wherein the base undergarment (200) further comprises a first leg extension (230) on the undergarment bottom (204) proximal to the undergarment first side (206), and a second leg extension (240) on the undergarment bottom (204) proximal to the undergarment second side (208), wherein the base undergarment (200) further comprises a first pocket (250) disposed on the undergarment front surface (212) proximal to the undergarment first side (206) on the first leg extension (230), and a second pocket (260) disposed on the undergarment front surface (212) proximal to the undergarment second side (208) on the second leg extension (240), wherein the first pocket (250) comprises a first pocket aperture (252) disposed on a bottom surface thereon, wherein the second pocket (260) comprises a second pocket aperture (262) disposed on a bottom surface thereon, wherein the base undergarment (200) further comprises a lower undergarment aperture (270) disposed at the undergarment bottom (204) between the first leg extension (230) and the second leg extension (240);
   b. a first diagonal catheter channel (300) disposed on the undergarment front surface (212), wherein a first open end is disposed on the undergarment first side (206) proximal to the undergarment top (202) and a second open end is disposed on the undergarment second side (208) proximal to the undergarment bottom (204);
   c. a second diagonal catheter channel (310) disposed on the undergarment front surface (212), wherein a first open end is disposed on the undergarment second side (208) proximal to the undergarment top (202) and a second open end is disposed on the undergarment first side (206) proximal to the undergarment bottom (204);
   d. a first vertical catheter channel (320) disposed on the undergarment front surface (212), wherein a first open end is disposed on the undergarment first side (206) proximal to the undergarment top (202) and a second open end is disposed on the undergarment first side (206) proximal to the undergarment bottom (204);
   e. a second vertical catheter channel (330) disposed on the undergarment front surface (212), wherein a first open end is disposed on the undergarment second side (208) proximal to the undergarment top (202) and a second open end is disposed on the undergarment second side (208) proximal to the undergarment bottom (204);
   wherein the first diagonal catheter channel (300) and the second diagonal catheter channel (310) are fluidly connected at an intersecting midpoint thereon, wherein the first open end of the first diagonal catheter channel (300) is fluidly connected to the first open end of the first vertical catheter channel (320) at an intersecting endpoint thereon, wherein the second open end of the first diagonal catheter channel (300) is fluidly connected to the second open end of the second vertical catheter channel (330) at an intersecting endpoint thereon, wherein the first open end of the second diagonal catheter channel (310) is fluidly connected to the first open end of the second vertical catheter channel (330) at an intersecting endpoint thereon, wherein the second open end of the second diagonal catheter channel (310) is fluidly connected to the second open end of the first vertical catheter channel (320) at an intersecting endpoint thereon;
   wherein the first diagonal catheter channel (300), the second diagonal catheter channel (310), the first vertical catheter channel (320) and the second vertical catheter channel form a catheter channel network (340);
   f. a length of catheter tubing (400) having a tubing first end (402) and a tubing second end (404), wherein the catheter tubing (400) is at least partially disposed within the catheter channel network (340), wherein the tubing first end (402) is adapted to connect to the user; and
   g. a fluid bag (410) having a fluid release (420) disposed on a lower portion of the fluid bag (410), wherein the fluid bag (420) is adapted to be enveloped by and disposed into the first pocket (250) or the second pocket (260), wherein the fluid release (420) extends through the first pocket aperture (252) or the second pocket aperture (262);
   wherein the medical urinary undergarment system (100) is effective for receiving and disposing of bodily fluid by the user;
   wherein for use, the user dons the base undergarment (200), wherein the user attaches the tubing first end (402) to a body opening, wherein the user routes the catheter tubing (400) through the catheter channel network (340), wherein the user connects the tubing second end (404) to the fluid bag (410), wherein the user places the fluid bag (410) into the first pocket (250) or the second pocket (260), wherein when the fluid bag (410) is filled with fluid, the user can drain the fluid bag (410) via the fluid release (420).

2. The system (100) of claim 1 wherein the base undergarment (200) comprises polyester, cotton, or a polyester and cotton blend.

3. The system (100) of claim 1, wherein the base undergarment (200) is adapted to resemble briefs.

4. The system (100) of claim 1, wherein the base undergarment (200) is adapted to resemble boxer shorts.

5. The system (100) of claim 1, wherein the base undergarment (200) is adapted to resemble spandex underwear.

6. The system (100) of claim 1, wherein the tubing first end (402) is adapted to connect to a urinary catheter.

7. The system (100) of claim 1, wherein the tubing first end (402) is adapted to connect to a percutaneous catheter.

8. The system (100) of claim 1, wherein the tubing first end (402) is adapted to connect to a Foley catheter.

9. The system (100) of claim 1, wherein the tubing second end (404) is adapted to connect to a plurality of fluid bags (410).

10. The system (100) of claim 1, wherein an access opening is disposed at the intersecting midpoint of the first diagonal catheter channel (300) and the second diagonal catheter channel (310), wherein an interior of the catheter channel network (340) can be accessed via the access opening (500).

11. The system of claim 10, wherein the access opening (500) is secured via a hook and loop system.

\* \* \* \* \*